United States Patent [19]

Mauvernay et al.

[11] 3,962,238

[45] June 8, 1976

[54] ETHERS OF N-PROPANOL AMINE

[75] Inventors: Roland Yves Mauvernay, Riom; Norbert Busch, Loubeyrat; Jacques Moleyre, Mozac; André Monteil, Gerzat; Jacques Simond, Chamalieres, all of France

[73] Assignee: Centre Europeen de Recherches Mauvernay "CERM", Riom, France

[22] Filed: Feb. 27, 1973

[21] Appl. No.: 336,357

[30] Foreign Application Priority Data

Mar. 6, 1972   France .............................. 72.07647

[52] U.S. Cl. .................. 260/247.2 B; 260/247.5 R; 260/293.79; 260/296 AE; 260/326.5 L; 260/326.5 R; 260/570.6; 260/570.9; 260/573; 424/248; 424/267; 424/274; 424/325

[51] Int. Cl.$^2$ ...................................... C07D 295/00
[58] Field of Search .............. 260/326.5 L, 247.2 B, 260/247.5 R, 293.76, 296 AE, 570.9, 570.6, 573

[56] References Cited

UNITED STATES PATENTS

| | | | |
|---|---|---|---|
| 2,600,301 | 6/1952 | Kerwin ............................. | 260/570.9 |
| 2,832,795 | 4/1958 | Hempel et al. .................. | 260/570.9 |
| 3,666,811 | 5/1972 | Van der Steldt ................. | 260/570.9 |

*Primary Examiner*—Paul J. Killos
*Attorney, Agent, or Firm*—Haseltine, Lake & Waters

[57] ABSTRACT

Ethers of n-propanolamine, preparation thereof and their use in treatment of cardiovascular conditions.

6 Claims, No Drawings

ETHERS OF N-PROPANOL AMINE

This invention relates to ethers of n-propanolamine, to the preparation thereof and to the use thereof.

The present invention provides an ether of an n-propanolamine having the general formula:

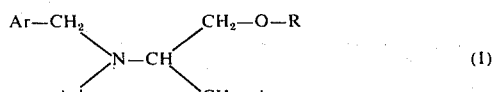

in which A is a tertiary aliphatic, cycloaliphatic or heterocyclic amino group, R is a straight or branched chain lower alkyl group or an aralkyl group, Ar is an aromatic group and $Ar^1$ is an aromatic or heterocyclic group, and addition salts thereof with pharmacologically acceptable acids.

When Ar and $Ar^1$ are both aromatic groups they may be like or unlike. Ar and $Ar^1$ may both be monocyclic aromatic groups and $Ar^1$ may be a heteromonocyclic group which may contain a nuclear nitrogen atom with or without an additional nuclear hetero atom.

The compounds of the present invention are useful as medicaments especially in the treatment of cardiovascular conditions.

In earlier patent applications we have described compounds having the general formula:

in which A and R have substantially the same meanings as in formula I above, and X respectively represents the following groupings in the various cases:

| | |
|---|---|
| —O—CO—Ar | French Special Medicine Patent No. 6571 M - 352 CAM |
| —N—CO—Ar<br>\|<br>H | French Special Medicine Patent No. 7700 M |
| OH<br>\|<br>—C—Ar<br>\|<br>$Ar^1$ | French Patent No. 70/00018 |
| H<br>\|<br>—C—Ar<br>\|<br>$Ar^1$ | French Patent No. 69/24645 |

Moreover, compounds having the following general formula are already known for their properties as antihistamines:

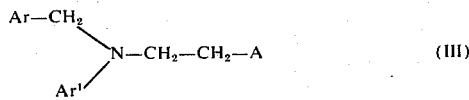

in which A has the same meaning as in the general formulae I and II above, whilst Ar and $Ar^1$ are aromatic groups. (Ehrhart/Ruschig Arzneimittel I, pages 208–210).

The compounds according to the present invention having the general formula I, are manifestly different from any of these groups of compounds.

The compounds of the present invention may be prepared from amino alcohols having the general formula:

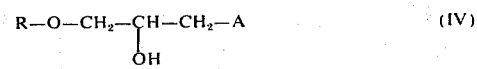

in which A and R are as defined above in connection with formula I.

In the first step of such preparation, the amino alcohols (IV), which are known materials, and are described inter alia in Belgium Pat. No. 718 425, are treated with thionyl chloride dissolved in a suitable solvent such as chloroform in order to obtain the corresponding chloro compounds having the general formula:

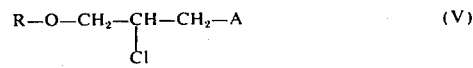

The latter compounds are then condensed with amines having the general formula

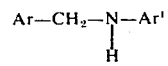

which have previously been converted to their sodium derivatives by reaction with sodium amide, to obtain the compounds of the present invention.

The invention also includes the addition salts of the compounds having the general formula I with pharmaceutically acceptable organic and inorganic acids such as hydrochloric acid and fumaric acid.

As an example of the process of the invention there will now be described the synthesis of 1-(3-isobutoxy-2-(phenylbenzyl)-amino)-propyl-pyrrolidino-hydrochloride (Compound No. 1).

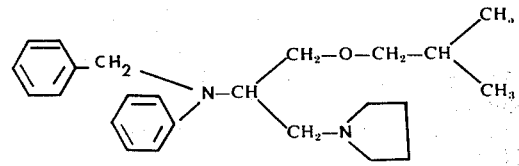

First step

Preparation of 1-(3-isobutoxy-2-chloro)propyl pyrrolidine

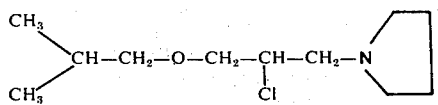

345 ml of thionyl chloride dissolved in 345 ml of chloroform are added, drop by drop, to 275 g of 1(3-isobutoxy-2-hydroxy)-propyl-pyrrolidine dissolved in 350 ml of chloroform, while maintaining the temperature at approximately 45°C. The reaction mixture is heated to reflux until gas is no longer evolved. The chloroform and the excess of thionyl chloride are removed under reduced pressure. The residue is poured on to 400 g of crushed ice. The reaction mixture is rendered alkaline with soda and the resulting mixture is extracted twice with 250 ml of diethyl ether. The combined ethereal extracts are dried over anhydrous sodium sulphate. After evaporation of the solvent the residue is distilled under reduced pressure: 220 g of product are obtained having the following properties:

Boiling point = 96°C/3 mm, $n_D^{24°}$ $c = 1,4575$,

Second step
Main product ml of diethyl ether. After the ether has been evaporated, the residue is distilled under reduced pressure and has Bpt = 184°C/0.1 mm, $n_D^{20} = 1.5538$.

77 g of the pure base in the form of a viscous liquid is thus obtained.

The hydrochloride, which is prepared in conventional manner, has a melting point of 128°C.

| Analysis | C% | H% | N% |
|---|---|---|---|
| Calculated: | 71.52 | 8.75 | 6.95 |
| Found: | 71.20 | 9.01 | 6.93 |

Table I which follows sets out a series of products according to the present invention which were obtained using the foregoing method but substituting the appropriate intermediates containing the desired groups R and A and Ar and Ar¹ respectively.

TABLE I

| COMPOUND No. | Ar | Ar' | R | A | Melting Points of Salts °C | C% Theory | C% Found | H% Theory | H% Found | N% Theory | N% Found |
|---|---|---|---|---|---|---|---|---|---|---|---|
| 1 | phenyl | phenylene | (CH₃)₂CH—CH₂— | pyrrolidinyl | Hydrochloride 128° | 71.52 | 71.20 | 8.75 | 9.01 | 6.95 | 6.93 |
| 2 | phenyl | phenylene | (CH₃)₂CH—CH₂— | pyrrolidinyl | Fumarate 150° | 67.08 | 66.90 | 7.66 | 7.20 | 8.69 | 8.75 |
| 3 | phenyl | phenylene | (CH₃)₂CH—CH₂— | (C₂H₅)₂N— | Fumarate 98° | 69.39 | 69.46 | 8.31 | 8.34 | 5.77 | 5.72 |
| 4 | phenyl | phenylene | CH₃— | pyrrolidinyl | Fumarate 155° | 68.16 | 68.42 | 7.32 | 7.30 | 6.35 | 6.31 |
| 5 | phenyl | phenylene | (CH₃)₂CH—CH₂ | morpholinyl | Fumarate 195° | 67.44 | 67.90 | 7.68 | 7.76 | 5.61 | 5.64 |
| 6 | phenyl | phenylene | phenyl—CH₂ | piperidinyl | Hydrochloride 133° | 74.55 | 74.05 | 7.82 | 7.40 | 6.21 | 6.14 |

23.4 g of sodium amide is added little by little to a solution of 92 g of N-benzylaniline in 500 ml of anhydrous xylene. The reaction mixture is then heated at 130° to 135°C for 6 hours.

Whilst maintaining the temperature at 110°C, 110 g of the product of the first step dissolved in 150 ml of xylene is added and the product heated for 6 hours at 120°C.

The product having been allowed to cool to ambient temperature, 200 ml of cold water are added. The organic phase is separated and extracted with an aqueous solution of hydrochloric acid.

After twice washing with 100 ml of diethyl ether, the aqueous phase is made alkaline with 50% caustic soda solution. The liberated base is twice extracted with 150

The pharmacological activity of the compounds of the invention in the cardiovascular field was determined on the dog in the manner described below:

An incision is made in the right-hand chest wall of an animal, which has been anaesthetised with chloralose and given artificial respiration, to enable the blood from the venus sinus to be drawn off and the apparatus required to record the following parameters to be inserted in position:

a. Output of the coronary sinus;
b. $P_aO_2$ of the blood from the coronary sinus; and
c. Amplitude of the contractions of the right ventricule.

At the same there were also measured:
d. Arterial pressure in a main carotid artery: and e. The rate of heart-beat determined cardiotachometrically.

Table II which follows records the determinations made of the various parameters, the results being expressed as a maximum percentage variation relative to the pre-treatment values.

The following Table III gives the average percentage inhibition of the cardiovascular effects of isoprenaline and of the cardiac effects of the stimulation of the right stellar ganglion.

TABLE III

|  | Number of animals | PERCENTAGE INHIBITION OF | | |
|---|---|---|---|---|
|  |  | Hypotension | Rate of Heart-beat | Positive inotropic effect |
| ISOPRENALINE (5 ug/kg Intravenous) | 4 | −54% | −32.7% | −46.5% |
| STIMULATION OF THE RIGHT STELLAR GANGLION | 3 |  | −30% | −21.3% |

These results show that a partial inhibiting effect is achieved as regards the β-adrenergic receptors at the

TABLE II

| COMPOUND No. | DOSE mg/kg. (intravenous) | NUMBER OF ANIMALS | CORONARY OUTPUT % | RATE OF HEART-BEAT % | SINUSAL $P_tO_2$ % | ARTERIAL PRESSURE % | AMPLITUDE OF VENTRICULAR CONTRACTION % |
|---|---|---|---|---|---|---|---|
| 1 | 2.5 | 7 | +51.2 | −28.6 | +119.2 | −39.8 | −0.7 |
|  | 5 | 7 | +36.9 | −31.8 | +120.8 | −40.2 | −22.3 |
| 2 | 5 | 3 | +55 | −28 | +71 | −43 | −25.5 |
| 3 | 5 | 4 | +117.8 | −19.2 | +158 | −30.5 | −3 |
| 4 | 5 | 4 | +110.5 | −14.5 | −56 | −26 | ÷17.5 |
| 5 | 5 | 3 | +24 | −3.5 | +11.6 | −15 | ÷1.5 |

These results show that, taken as a whole, the products under examination have the ability to increase the output of coronary blood, to reduce the rate of heart beat and especially, with the exception of compound No. 4, to increase the oxygen content of the venous cardiac blood. The latter action is demonstrated by an excess in the supply of oxygen relative to the requirements of the myocardium. The arterial pressure is also lowered for a short time. In most cases there is little alteration in the ventricular inotropism.

Particular note should be taken, in the case of compound No. 1, of the very considerable increase in the oxygen content of the venous cardiac blood in relation to the increase in coronary output, which may be simply attributed to the improved circulation of the blood. The extremely slow rate of heart-beat brought about by the products certainly plays an important role in this respect.

It then seemed interesting, using compound No. 1, to seek the existence of an action on the β-adrenergic receptors in the manner outlined below:

A stimulating electrode was placed in position on the right stellar ganglion of dogs anaesthetised as described above and for which there were recorded:
 a. The arterial pressure,
 b. Ventricular inotropism (the amplitude of contraction of the right ventricle), and
 c. The rate of heart-beat.

The chest of the animals were not open and they were breathing freely.

The β-adrenergic receptors, both cardiac and vascular, were stimulated by electrical stimulation of the right stellar ganglion or by intravenous injection with isoprenaline (5 μg/kg). The measurements were taken both before and after administration of compound No. 1 by the intravenous route in a dose of 5 mg/kg bodyweight.

cardiovascular level of treatment.

In conclusion, it is apparent that the members of the series of compounds possess a distinct cardio-vascular activity which is manifested by an improvement in circulation by the enhanced oxygenation of the myocardium in consequence of a slow rate of heart-beat.

In addition to the general properties of the compounds of the present invention, compound No. 1 is also of interest in that it also possesses inhibiting effects with respect to the stimulation of the β-adrenergic receptors.

The pharmacological activities of the compounds having the general formula I thus enable their application in human therapy to be anticipated, as medicaments intended for treating particularly:
 Myocardiac anoxaemia,
 Coronary deficiencies, angina pectoris,
 Infarction of the myocardium, and
 Cardiac deficiencies associated with coronary circulatary trouble.

When admixed with the usual excipients, they may be administered orally or rectally, in daily doses of between 100 and 800 mg.

What we claim is:

1. An ether of n-propanolamine having the formula

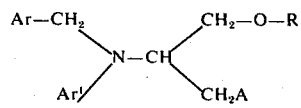

wherein A is morpholino, pyrrolidino, piperidyl, and di-lower-alkyl amino, R is a straight or branched chain lower alkyl, or benzyl, Ar is aryl and $Ar^1$ is aryl or pyridyl, and pharmacologically acceptable salts thereof.

2. The ether of claim 1 in which A is pyrrolidino, R is isobutyl and Ar and Ar¹ are both phenyl, and the hydrochloride thereof.

3. The ether of claim 1 in which A is pyrrolidino, R is isobutyl, Ar is phenyl and Ar¹ is 2-pyridyl, and the acid fumarate thereof.

4. The ether of claim 1 in which A is diethylamino, R is an isobutyl and Ar and Ar¹ are both phenyl, and the acid fumarate thereof.

5. The ether of claim 1 in which A is morpholino, R is isobutyl and Ar and Ar¹ are both phenyl and the acid fumarate thereof.

6. The ether of claim 1 in which A is piperidyl, R is benzyl and Ar and Ar¹ are both phenyl and the hydrochloride thereof.

* * * * *